(12) United States Patent
Zwart

(10) Patent No.: US 12,370,007 B2
(45) Date of Patent: Jul. 29, 2025

(54) ASSEMBLY COMPRISING A TRANSFER TOOL, AND TRANSFER TOOL

(71) Applicant: ROVERS VASTGOED B.V., Oss (NL)

(72) Inventor: Meindert Durk Zwart, Oss (NL)

(73) Assignee: ROVERS VASTGOED B.V., Oss (NL)

( * ) Notice: Subject to any disclaimer, the term of this patent is extended or adjusted under 35 U.S.C. 154(b) by 762 days.

(21) Appl. No.: 17/636,647

(22) PCT Filed: Aug. 19, 2020

(86) PCT No.: PCT/EP2020/073221
§ 371 (c)(1),
(2) Date: Feb. 18, 2022

(87) PCT Pub. No.: WO2021/032788
PCT Pub. Date: Feb. 25, 2021

(65) Prior Publication Data
US 2022/0401172 A1    Dec. 22, 2022

(30) Foreign Application Priority Data

Aug. 20, 2019 (NL) ..................... 2023671

(51) Int. Cl.
*A61B 50/20* (2016.01)
*A61B 10/00* (2006.01)
*A61B 10/02* (2006.01)

(52) U.S. Cl.
CPC .......... *A61B 50/20* (2016.02); *A61B 10/0096* (2013.01); *A61B 10/02* (2013.01)

(58) Field of Classification Search
CPC ..... A61B 50/20; A61B 10/0096; A61B 10/02; A61B 2010/0074; A61B 2010/0216;
(Continued)

(56) References Cited

U.S. PATENT DOCUMENTS 6,719,691 B2 * 4/2004 Kritzman ........... A61B 10/0096
600/362
2016/0302776 A1 * 10/2016 Adolphson ........ A61B 10/0096

FOREIGN PATENT DOCUMENTS

WO   WO-2017077415 A1 *  5/2017  ......... A61B 10/0045
WO   WO-2017209628 A1 * 12/2017  ......... A61B 10/0096

* cited by examiner

*Primary Examiner* — Ariana Zimbouski
*Assistant Examiner* — Eric Rassavong
(74) *Attorney, Agent, or Firm* — Davis Wright Tremaine LLP; Heather M. Colburn

(57) ABSTRACT

The invention relates to an assembly comprising a sampling device with a rod and a swab and a transfer tool for detaching the swab from the rod and transferring the detached swab to a container. The transfer tool comprises a housing enclosing a closed chamber having a swab-member passage and configured for receiving the swab-member. The housing comprises a first housing part and second housing part hinged to the first housing part. The first housing part and second housing part define an entry opening to a channel delimited by the first and second housing part. This channel extends from outside the housing to the passage. The first housing part and second housing part are rotatable around the hinge between a holding condition and a non-holding condition. The swab-member passage is configured to prevent, in holding and non-holding condition, the base from entering the passage whilst allowing, in non-holding condition, the swab member to pass through the passage. The channel and swab are configured to allow, in non-holding condition, inserting the swab-member and the base through the entry opening into the channel, advancing the swab-member to and through the passage into the chamber until the passage prevents the base from entering the passage, and to prevent, in holding condition whilst the passage blocks the base in the insertion direction and the swab-member (Continued)

projects through the passage into the chamber, the base from movement opposite to the insertion direction.

19 Claims, 14 Drawing Sheets

(58) Field of Classification Search
CPC ............ A61B 10/0045; A61B 10/0051; B01L 2300/0609; B01L 2300/043; A61F 13/38
See application file for complete search history.

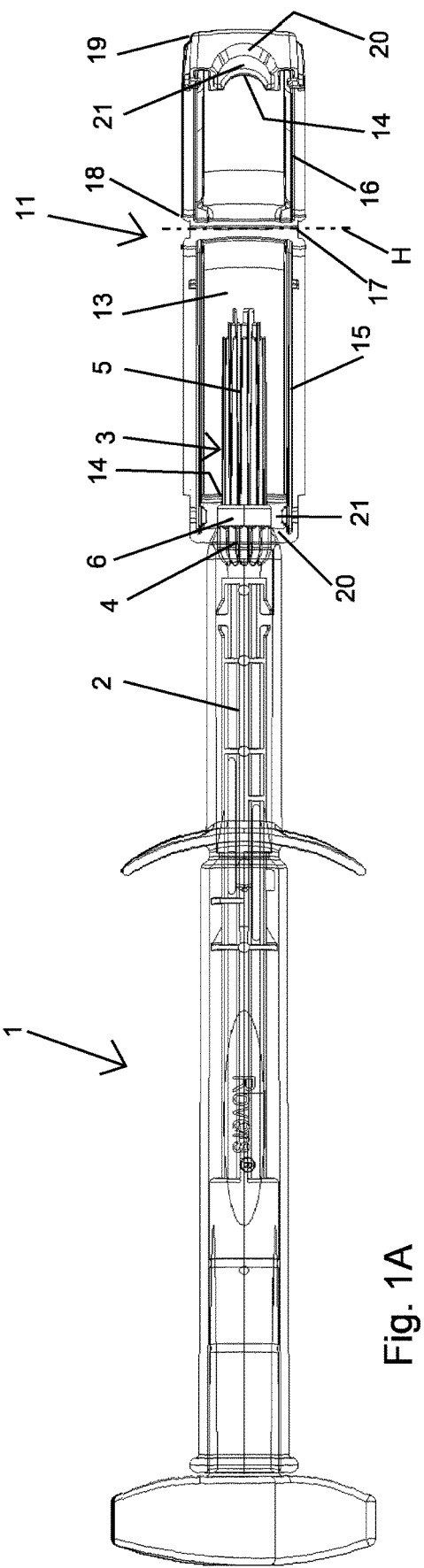
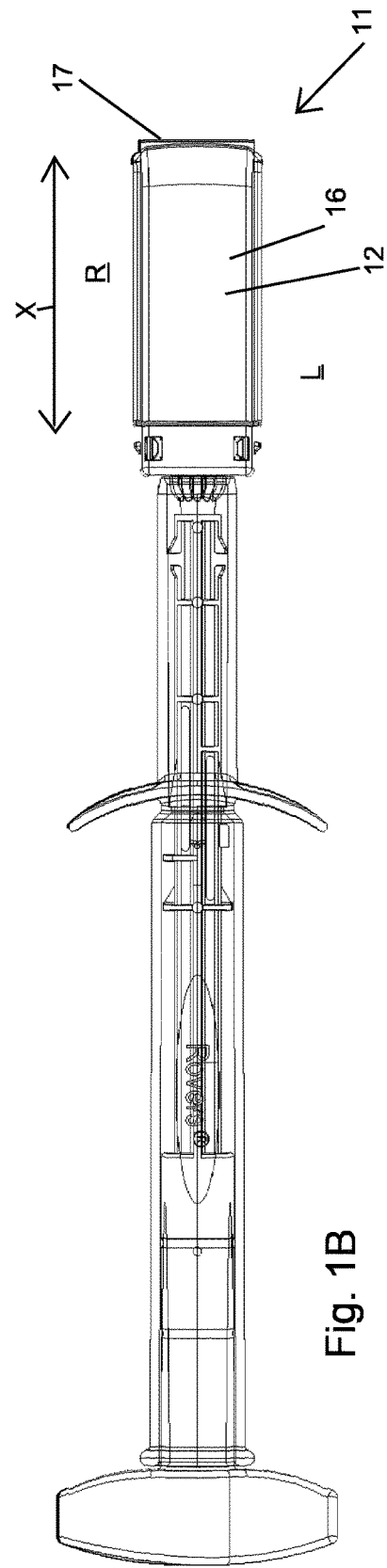
Fig. 1A
Fig. 1B

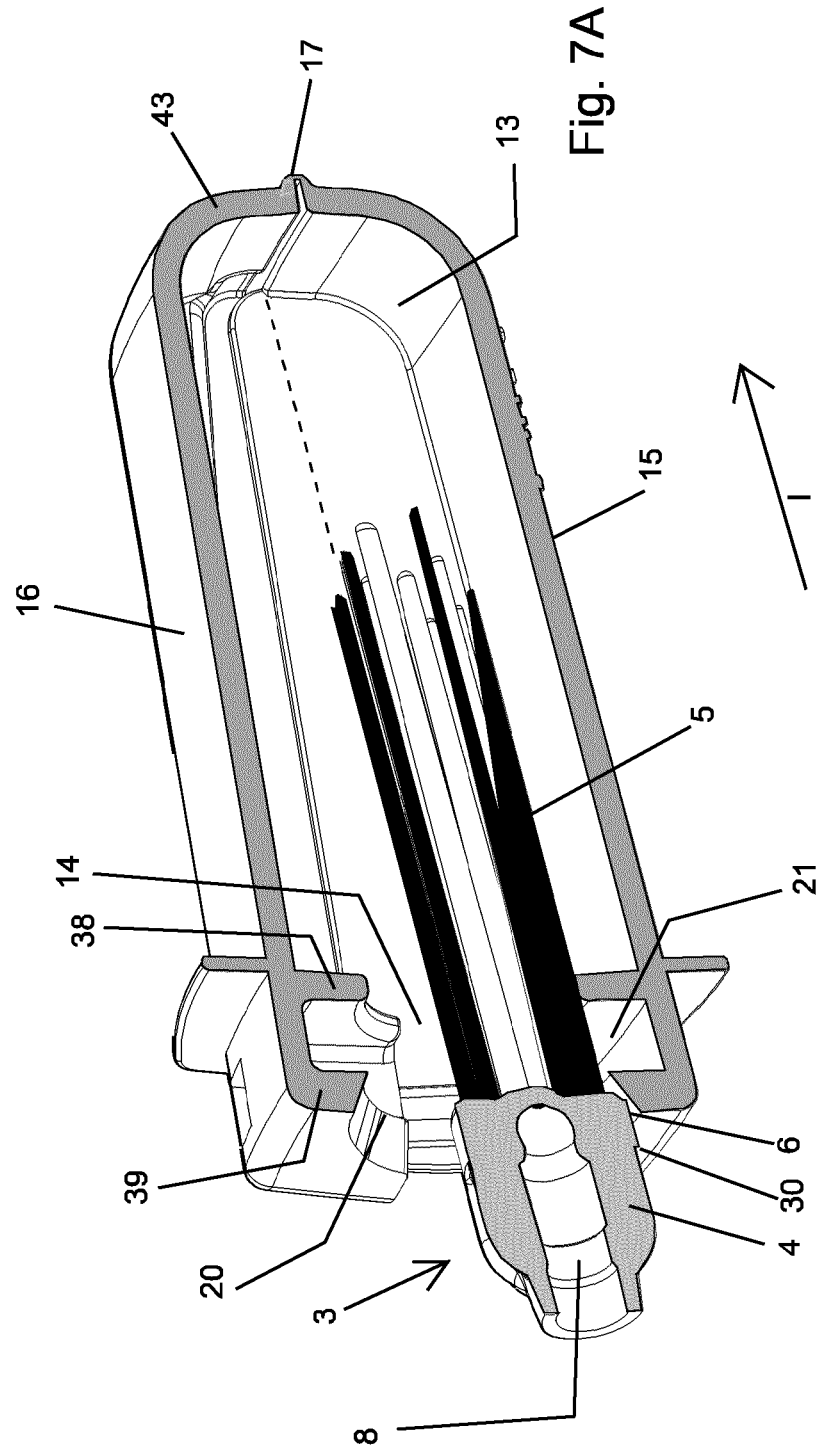

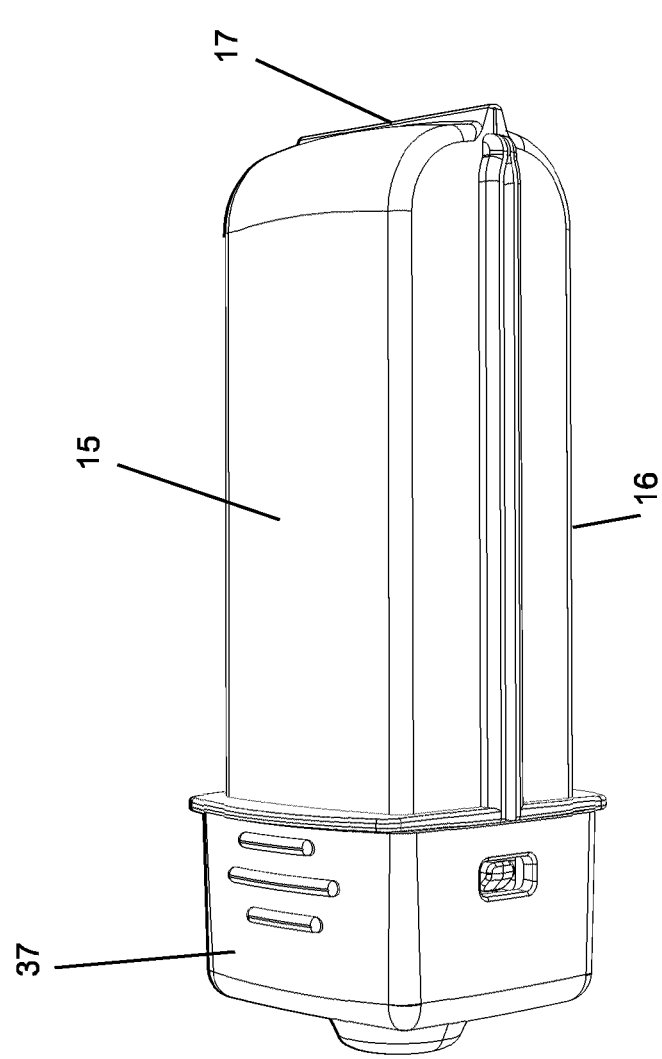

ASSEMBLY COMPRISING A TRANSFER TOOL, AND TRANSFER TOOL

CROSS-REFERENCE TO RELATED APPLICATIONS

The present application is a U.S. National Stage entry under 35 U.S.C. § 371 of International Patent Application No. PCT/EP2020/073221, filed on Aug. 19, 2020, designating the United States of America and published in English on Feb. 25, 2021, which in turn claims priority to Netherlands Patent Application No. NL 2023671, filed on Aug. 20, 2019, each of which is hereby incorporated by reference in its entirety.

TECHNICAL FIELD

The present invention relates to a transfer tool for detaching a swab from a rod and transferring the detached swab to a container. The swab and rod are part of a sampling device for sampling human tissue and/or cell material, for example for harvesting human tissue and/or cell material in a body cavity. Such a body cavity may for example be the vagina and/or cervix; the anus; or the mouth and/or throat.

BACKGROUND

In the prevention and early or late detection of cancer of the cervix, vulva, vagina, penis, anus, mouth or throat, a first step is often to obtain a sample from the cervix, vulva, vagina, penis, anus, mouth, throat or possibly a combination of one of more of these, followed by examining the sample obtained for the presence of HPV (=Human PapillomaVirus). In case positive for HPV, this does not necessarily mean there is one of the mentioned cancers, but—as it is presently believed—one of these cancers without being HPV positive is not possible. So the HPV test is in general a first test to determine whether further examination is necessary.

Taking a sample may as such be done in different manners, one of these manners is by means of a swab. A swab in general as well as according to the invention is a device having a swab-member which collects sample by collecting tissue and/or cell material in the swab-member. This collecting may for example be by absorption, like cotton of a cotton bud (or Q-tip™) does, or by capillary action like between parallel hairs, or by grabbing tissue and/or cell material between hairs, and or in similar manner, or a combination of one or more these. A swab member in general and according to the invention comprises an absorbing member and/or a plurality of hairs. Examples of sampling devices with a swab having a swab-member with plurality of hairs are according to the invention for example the Cervex-Brush®, the Cervex-Brush® Combi, the Endo-Cervex-Brush®, the EndoCervex-Brush®-S, the Orcellex® Brush, the Annex® Brush, the Viba-Brush®, and the Evalyn® Brush, which are all marketed by Rovers Medical Devices B.V. (NL), see https://www.roversmedicaldevices.com/cell-sampling-devices/. In all these sampling devices, a swab is mounted on a rod. The Viba-Brush® and the Evalyn® Brush have in fact an about similar swab-member having for example 20 to 50, such as about 26 mutually about parallel plastic thread like fibres extending axially from a base mounted on a rod extending in the same axial direction.

The swab-sample is taken at one location and the examination for HPV takes place in a laboratory, which means that the swab with sample obtained is to be transferred from the patient to the laboratory. This transfer in general comprises transporting. The entire sampling device may be transported to the laboratory for further examination, but it is also conceivable to transport only the swab containing the sample. In the latter case, the swab is to be removed from a rod of the sampling device and subsequently to be sent to the laboratory. When removing the swab and sending the swab, it is of importance that no harvested sample is lost. Further contamination of the harvested sample is to be prevented. This may be achieved by removing the swab from the rod by means of a tongs, like a pincette or forceps, and subsequently putting the swab in a transportation container which is subsequently closed. After having arrived at the laboratory, the swab is to be removed from the container and may be put in a container for further examination in the laboratory. In this examination a liquid may be added in the container to dislodge harvested tissue and/or cell material from the sample-member and subsequently a pipette or similar device may be used to taken some of the liquid with dislodged tissue and/or cell material for the actual examination. The above is doable, but only in for trained persons and it is relatively complex and time consuming. Further it is not doable in case of self-sampling by the patient him/herself at home, like for example with the Evalyn® Brush which is specifically designed for the purpose of self-sampling at home.

In the prevention and early detection of cancer of the cervix and vagina, women of certain age are invited to participate in population screenings. Not all woman invited show up. Not showing up may have various reasons. In order to reach also woman not showing up, self-sampling devices, like the Evalyn® Brush, have been developed. These sampling devices may be send to these woman and after a sample having been taken the respective woman can return the sampling device to the laboratory.

When a sampling device with swab still attached to the rod arrives at the laboratory, a similar problem may arise with respect to removing the swab from the rod as is manifest when removing the swab from the rod before sending it to the laboratory. At laboratory, persons trained for removal of the swab by means of a tongs may be present, but it is still a delicate task in order to avoid loss of harvested tissue and/or cell material and to prevent contamination.

SUMMARY

The present invention has as its object to solve one or more of the above problems.

This object is according to a first aspect of the invention achieved by providing an assembly comprising:
 a sampling device comprising a rod and a swab, wherein the swab comprises a base and a swab-member integral with the base, the base being mounted on the rod and between the rod and the swab-member, the sampling device being configured to allow detachment of the swab from the rod preferably in a longitudinal direction of the rod;
 a transfer tool for detaching the swab from the rod and transferring the swab—detached from the sampling device—to a container or a location.

The time between detaching the swab from the rod and transferring the swab from the transfer to a container or other location may be short, like in the order of seconds or minutes, or long, like in the order of days or weeks. In case the time between said detaching and said transferring is long, the transfer tool may also serve as storage device in which the swab is transported to for example a laboratory.

The swab may be transferred into a tubular container. Instead of transferring the swab to or into a container, such as a tubular container, the swab may also be transferred to some desired location.

The transfer tool according to the invention comprises a housing enclosing an essentially closed chamber, which closed chamber is accessible through a swab-member passage and configured for receiving the swab-member. The swab-member passage is always open and only obstructed when a swab-member is in the passage. The housing comprises a first housing part and second housing part hinged to the first housing part by a hinge arranged at a first side of the second housing part. The first housing part and second housing part define, at a second side of the second housing part opposite the first side, an entry opening into a channel delimited by the first and second housing part. This channel extends from outside the housing to the swab-member passage to allow the swab-member to be introduced into the housing and into the chamber.

The first housing part and second housing part are rotatable, around a hinge axis of the hinge, with respect to each other to move between a holding condition and a non-holding condition.

The swab-member passage is configured to prevent, in the holding condition as well as the non-holding condition, the base from entering the swab-member passage whilst allowing, in the non-holding condition, the swab member to pass through the swab-member passage. The channel and swab are configured:

- to allow, in the non-holding condition, inserting the swab-member and the base, in an insertion direction, from outside the housing through the entry opening into the channel, advancing the swab-member, in the insertion direction, to and through the swab-member passage into the chamber until the swab-member passage prevents the base from entering the swab-member passage, and
- to prevent, in the holding condition whilst the swab-member passage blocks the base in the insertion direction and the swab-member projects through the swab-member passage into the chamber, the base from movement into a direction opposite to the insertion direction.

The transfer tool according to the invention allows the swab to be inserted into the housing with its swab-member projecting into the chamber, which is except for the swab-passage essentially closed. After having inserted the swab into the housing with the swab-member projecting into the chamber, the first and second housing part may be moved from the non-holding condition to the holding condition in which the base is engaged or grasped by the first and second housing part. This closing may simply be by squeezing the first and second housing part between two fingers. Next, with the first and second housing part in the holding condition the rod may be pulled away from the swab and housing to disconnect the rod from the swab. The connection between the swab and rod which is to be disconnected, may be a male-female-connection like a screwed or clamping male-female-connection. The connection to be disconnected may also be another type of connection requiring some manipulation or force to disconnect the connection. The housing provides so to say a gripper having a chamber in which the swab-member is shielded from the environment and having a section with which the base is grasped. The passage being configured to act as a stop for the base in the non-holding as well as the holding condition, prevents swab and the swab-member from being inserted too far. Inserting too far may result in sample harvested with the swab-member being dislodged in the chamber and subsequently being left behind in the chamber and being lost for further examination. Further, inserting too far may result in the swab getting stuck in the housing and preventing this ensures that the swab can be easily released without being kept stuck inside the tool.

Calling the swab-member of the swab the 'head' and calling the base of the swab the 'tail', the insertion of the swab into the tool is so to say 'head-first'. The configuration of the tool ensures that, in holding condition, the swab inserted is kept, relative to the tool, in the same condition as in which it has been inserted. This in turn ensures that, when releasing the swab from the tool, the swab will exit the tool so to say 'tail-first'. This allows for an accurate manipulation of swab when releasing it. The swab can be precisely released from the tool with the swab orientated in an orientation known beforehand. For example when the tool is, in holding condition, placed on top of a tubular container with the entry opening of the tool facing downwardly into the tubular container, the swab will be deposited into the tubular container with the base down and the swab-member projecting upwardly from the base. This ensures that, during further processing, the swab-member can be easily reached from through the open end of the tubular container and/or it prevents that for example a pipette is inadvertently inserted into the opening in the base (which opening served as female connection part which before disconnecting from the rod received the male connection part of the rod).

According to a further embodiment of the first aspect of the invention, the housing has a length direction which extends from the first side to the second side, and which defines a length of the chamber. In this embodiment, the first housing part has, at a right side of the chamber, a right side wall extending in the length direction perpendicular to the hinge axis and, at a left side of the chamber, a left side wall extending in the length direction perpendicular to the hinge axis;

and correspondingly the second housing part has, at a right side of the chamber, a right side wall extending in the length direction perpendicular to the hinge axis and, at a left side of the chamber, a left side wall extending in the length direction perpendicular to the hinge axis. To allow hinging of the first and second housing part between the non-holding and holding condition, on the one hand, and to ensure the chamber being closed in the holding condition as well as in the non-holding condition, on the other hand, the right side wall of the first housing part and the right side wall of the second housing part overlap and continuously lie against each other along the full length of the chamber to provide a contact seal in the non-holding as well as in the holding condition; and similarly, the left side wall of the first housing part and the left side wall of the second housing part overlap and continuously lie against each other along the full length of the chamber to provide a contact seal in the non-holding as well as in the holding condition.

According to a further embodiment of the above embodiment with contact seals, the assembly according to the first aspect of the invention, the left and right side wall of one of the first and second housing part may, viewed transverse to the length direction, be arranged between the left and right side wall of the other of the first and second housing part. This arrangement prevents the first and second housing part from movement with respect to each other in a direction parallel to the hinge-axis.

According to another further embodiment of the above embodiment with contact seals, a kind of labyrinth sealing may be obtained by providing:
- the right side wall of one of the first and second housing part with a right support face, which projects from that side of the respective side wall facing the overlapping right side wall of the other of the first and second housing part, which right support surface is configured to lie:
  - when in the holding condition, along the full length of the chamber continuously against a right length edge of the right side wall of the other of the first and second housing part, and
  - when in the non-holding condition, at a distance from the right length edge, and
- the left side wall of one of the first and second housing part similarly with a left support face, which projects from that side of the respective side wall facing the overlapping left side wall of the other of the first and second housing part, which left support surface is configured to lie:
  - when in the holding condition, along the full length of the chamber continuously against a left length edge of the left side wall of the other of the first and second housing part, and
  - when in the non-holding condition, at a distance from the left length edge.

According to another further embodiment of the first aspect of the invention, the grasping of the base in holding condition may achieved by configuring the channel and base to prevent, when in holding condition, the base from movement into the direction opposite to the insertion direction by at least part of the base being clamped inside the channel. Alternatively or additionally, be achieved by configuring:
- the base to have a wide section which, in the direction away from the swab-member, reduces in wideness with a step,
- the channel to widen, viewed from the outside into the channel, behind the entry opening to a size allowing the wide section to be received, optionally to a size larger than the wide section,
- the entry opening to have, in the non-holding condition, a size wider than the wide section to allow the base to pass through the entry opening, and
- the entry opening to have has, in the holding condition, a size smaller than the wide section, in order to preventing the wide section of the base, when it is in the channel and when the tool is in the holding condition, from passing through the entry opening in a direction opposite to the insertion direction.

According to still another further embodiment of the first aspect of the invention, the movement between the non-holding and holding condition may be defined by providing the tool with a slit-protrusion-system comprising a slit and a protrusion projecting into the slit, wherein the slit extends in a direction transverse to the hinge axis and transverse to the length axis, wherein the protrusion extends in a direction parallel to the hinge axis, and wherein the protrusion is movable to and fro through the slit between a first end of the slit defining to the non-holding condition and a second end of the slit defining the holding condition, and wherein one of the first and second housing part is provided with the slit whilst the other of the first and second housing part is provided with the protrusion.

According to a further embodiment of the embodiment with a slit-protrusion system, the tool comprises two of said slit-protrusion systems, one of said slit-protrusion-systems being provided on a right side of the housing and the other of said slit-protrusion-systems being provided on the left side of the housing, wherein right and left is defined with respect to a direction transverse to the hinge axis. Two slit-protrusion systems, one on either side of the housing provide the tool stability and prevents the first and second housing part from being jammed with respect to each other.

According to another further embodiment of the embodiment with a slit-protrusion system, the bottom of the slit may be provided with a bump configured to hinder the protrusion, when it is at the second end of the slit, from movement towards the first end of the slit such that the protrusion is prevented from leaving the second end unless a predetermined force is applied to force the protrusion to pass the bump. When moving from the non-holding condition to the holding condition, the bump allows the protrusion to pass upon exerting a sufficient closing force and subsequently to snap behind the bump. Once snapped behind the bump, the first and second housing are maintained in their holding condition to ensure the housing being closed and preventing the swab contained in the housing from releasing out of the housing and from being contaminated by the outside environment. The first and second housing part may be released from the snapped holding condition by exerting a predetermined force to force the protrusion to pass the bump in opposite direction towards the non-holding condition. It is noted here that the function of the bump is primarily to keep the housing in closed condition once the swab received in the housing is detached from the rod. The predetermined force required to force the protrusion to pass the bump towards the non-holding condition may be:
- relatively low such that, when detaching the swab from the rod, squeezing—for example between two finger or by a tongs—the first housing part and second housing part towards the holding condition is necessary to prevent 'the protrusion from passing the bump in the direction of the non-holding condition' which may result in the swab from being withdrawn or released from the housing; or
- relatively high such that the first housing part and second housing part may stay in their holding condition (without any additional squeezing) whilst the swab is being detached from the rod.

According to still another further embodiment of the embodiment with a slit-protrusion system, the tool may comprise a tensioning element configured to build up a force between the first housing part and second housing part when the first housing part and second housing part are moved from the non-holding condition to the holding condition, which force acts in a direction to return the first and second housing parts to their non-holding condition. This may facilitate opening of the tool from the holding to the non-holding condition. It may facilitate to use the tool as a kind of tongs which automatically opens upon release of a squeezing force closing the housing.

According to still another further embodiment of the first aspect of the invention, the entry opening may, viewed from the outside into the channel, be tapered at its outside. This taper may facilitate placing the tool on a tubular container for releasing the swab into the tubular container with the base of the swab facing the bottom of the container and the swab-member facing away from the bottom of the container. In order to close convert the tool in a closed receptacle, the assembly may, according to still another further embodiment of the first aspect of the invention, comprise a cap delimiting a cavity configured to receive the end of the housing with the entry opening when the housing is in holding condition and to keep the housing in holding condition when said end of the housing has been inserted into the cavity. This cap may also prevent the first and second housing part from inadvertently returning to the non-holding condition. According to a further embodiment of this embodiment, the cavity may—in order to prevent the cap from tilting on the housing when removing the cap—have
- a depth and a width with a ratio of the depth to the width is at least 50%, such as at least 60%; and/or
- a depth of at least 7 mm, such as at least about 8 or about 9 mm.

According to still another further embodiment of the first aspect of the invention, the container may be a tube with closed bottom and open top end.

According to still another further embodiment of the first aspect of the invention, the swab-member passage is delimited by both a part of the first housing part and a part of the second housing part and is configured to have in the holding condition a size smaller than in the non-holding condition such that the swab-member passage engages a part of the swab-member extending within the passage. This engagement provides a kind of sealing of the wall of the swab-member passage onto the part of the swab-member close to the base.

According to a second aspect of the invention, one or more objects of the invention are achieved by providing a transfer tool for detaching a swab from a rod and transferring the detached swab to a container, wherein the transfer tool is configured according to the transfer tool of the assembly according to the first aspect of the invention.

BRIEF DESCRIPTION OF THE DRAWINGS

According to a third aspect of the invention, one or more of the objects of the invention are achieved by providing a transfer tool configured for use in an assembly according to the first aspect of the invention.

Embodiments of the invention are shown in the figures. In the figures:

FIGS. 1A and 1B show a plan view of a first embodiment of an assembly according to the invention; FIG. 1A showing the transfer tool in an unfolded condition, which is a non-use condition which shows the inner side of the tool; and in which FIG. 1B showing the transfer tool in a use condition.

FIG. 2A showing the tool in a non-holding condition in which the swab is allowed to be inserted; FIG. 2B showing the tool in the holding condition before disconnecting the rod; and FIG. 2C showing the tool in holding condition after disconnecting the rod;

FIG. 3A showing the tool in a non-holding condition in which the swab is allowed to be inserted; FIG. 3B showing the tool in the holding condition before disconnecting the rod; and FIG. 3C showing the tool in holding condition after disconnecting the rod;

FIG. 4A showing the assembly according to the invention before release and FIG. 4B showing the assembly after release;

FIGS. 7A and 7B show a perspective cross section of an assembly according to the invention as shown in FIGS. 1A-6; FIG. 7A showing the transfer tool in the non-holding condition during insertion of a swab; FIG. 7B showing the transfer tool in the holding condition after insertion of the swab; and FIG. 8 shows a perspective view of an assembly of transfer tool and swab, as is shown in the FIGS. 1A-7B, wherein the transfer tool is provided with a cap.

In FIGS. 1A-8 same reference numbers and signs have been used for corresponding parts of different embodiments. Taking into account the similarities throughout the FIGS. 1A-8, the reference numbers and signs used have not been repeated in all figures to prevent the figures being crowded by reference numbers/signs. But taking into account the similarities at face by looking to the figures it will be clear that each figure may easily be supplemented with corresponding reference numbers.

DETAILED DESCRIPTION

Figure 2A:
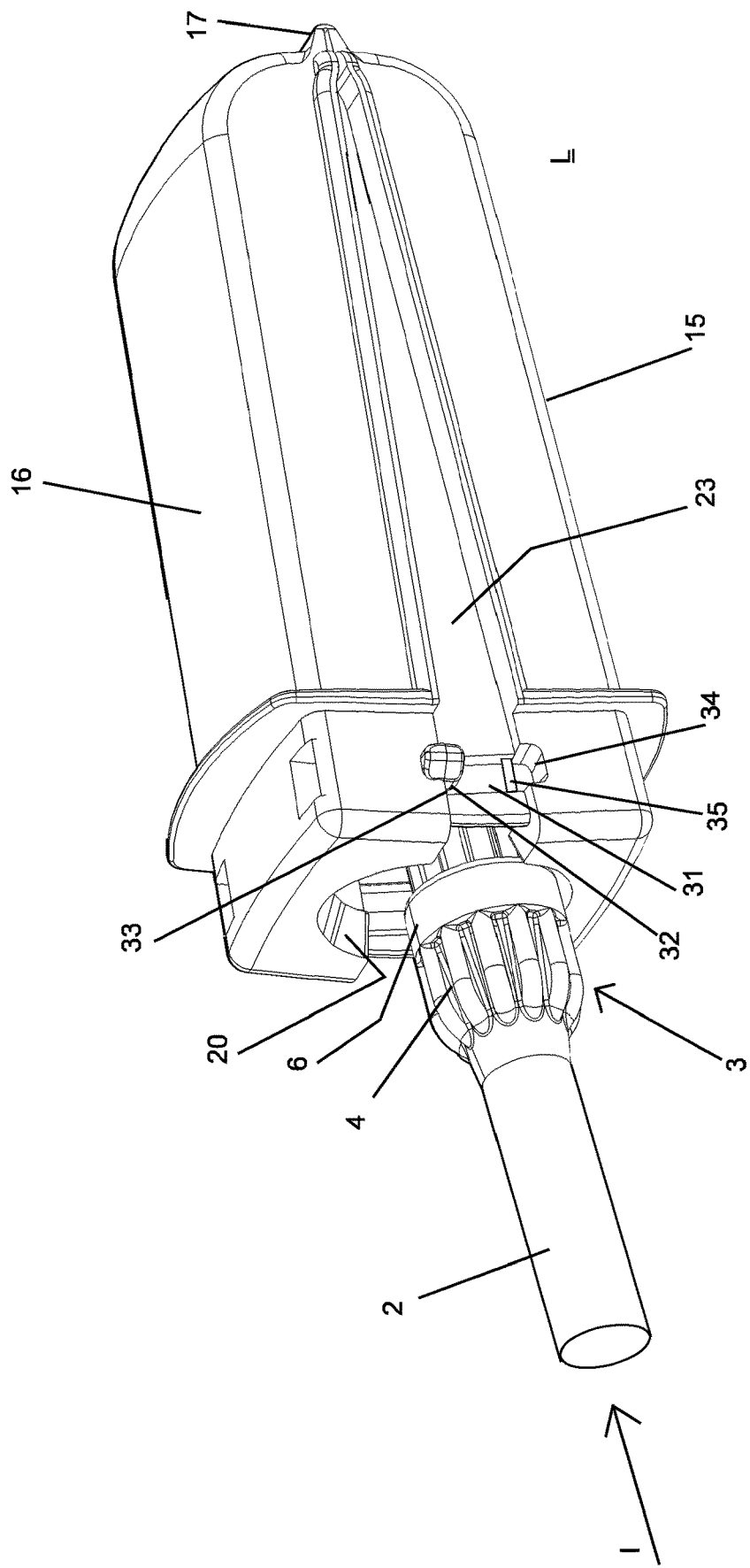
FIGS. 2A-2C show perspective views of a second embodiment of an assembly according to the invention.

FIG. 1 shows in plan view an assembly according to the invention. This assembly comprises a sampling device 1 and a transfer tool 11.

The sampling device 1 is in the embodiment of FIG. 1 a sampling device according to WO-2011/021931 marketed under the name Evalyn® Brush. This sampling device 1 may be used for self-sampling, i.e. a woman may use this sampling device to harvest a sample material from the vagina and/or cervix, followed by sending the swab with harvested sample to a laboratory for, for example, HPV-examination. Presently, the entire sampling device 1 is send to the laboratory.

For a detailed description of the sampling device 1, reference is made to WO-2011/021931. In short, the sampling device 1 comprises three components: a tube—in FIG. 1 a transparent tube—, a rod 2, and a swab 3. The swab 3 is mounted on one end of the rod 2 by means of a clamping male-female-connection. The swab comprises a base 4 and a swab-member 5 integral with the base 4. The swab-member 5 comprises a plurality of in this example 26 about parallel axial hairs or filaments between which sample material is collected when sampling. It is noted that the number of parallel hairs may also be different from 26, it may in fact be any number of parallel hairs. The base 4 may have a wide section 6 which is wider than the rest of the base. The wide section 6 is however not required. Further, it is to be noted here, that:
- the swab-member 5 formed by the plurality of about parallel axial hairs may according to the invention any other type of swab-member, like a cotton swab or any other absorbing swab, or a swab-member configured for grabbing sample material; and
- the male-female connection may be any other type of detachable connection, like a snap connection or connection with a weakened breakable part.

The transfer tool 11 is designed for removing the swab 3 from the rod and subsequently transferring the swab 3 to a container 40 (see FIG. 4) or any other location. Removing the swab 3 from the rod 2 may be done in a laboratory, by a trained person, or by the patient herself. In the latter case, the transferring of the swab may include sending the swab by mail to the laboratory. In the first case, the transfer may be in the laboratory from the rod to the container or any other place.

FIG. 1B shows the transfer tool 11 in a use condition, FIG. 1A shows the transfer tool in a non-use condition which may for example occur during fabrication of the transfer tool 11. In the non-use condition of FIG. 1A, the transfer tool is so to say folded open to show the interior of the transfer tool 11.

As shown in FIG. 1 and the other FIGS. 2-8 as well, the transfer tool 11 comprises a housing 12 having a first housing part 15 and second housing part 16 attached to the first housing part 15 by a hinge 17. This hinge 17 allows for rotation of the first housing part 15 with respect to the second housing part 16 around a hinge axis H. The second housing part 16 has a first side 18 where it is hinged by the hinge 17 to the first housing 15 and a second side 19 opposite the first side 18.

The housing 12 encloses a chamber 13, which in a use condition, is essentially closed except for a swab-member passage 14. The swab-member passage 14 is configured such that the swab-member 5 may pass through it whilst, in all use condition(s) like shown in FIG. 1B and the FIG. 1-8, the base 4 of the swab 3 is stopped by the swab-member passage 14. This may for example be realized by designing the passage 14 with smaller cross-sectional dimensions than the base 4. The passage 14 is formed in a front wall of the chamber 13. This front wall may be made of one piece attached to either the first housing part 15 or the second housing part 16, or it may be made of two wall parts, one attached to the first housing part 15 and the other to the second housing part 16, which housing parts both define a part of the swab-member passage 14.

At the second side 19 of the second housing part 16, the first housing part 15 and second housing part 16 define an entry opening 20 to a channel 21, which extends from outside the housing 12, as from the entry opening 20, to the swab-member passage 14. This channel 21 is delimited by the first housing part 15 and second housing part 16.

Instead of a sampling device 1 as shown in FIG. 1, also another sampling device may be used, for example a sampling device marketed as Vibra-Brush® or any other swab-based sampling device may be used. Therefore, the sampling device is in FIGS. 2-8 schematically represented by means of the rod 2.

Figure 5:
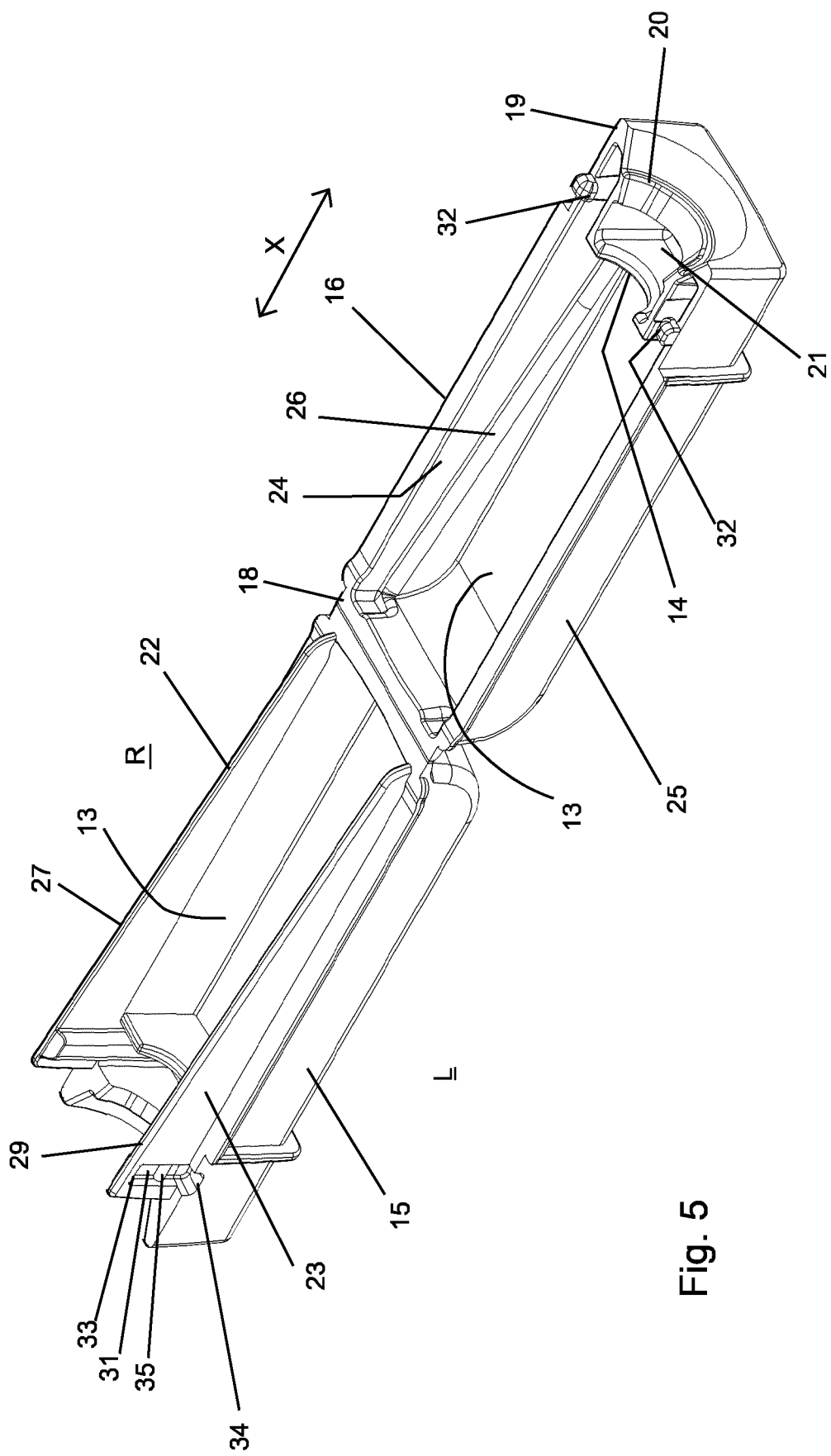
FIG. 5 shows a perspective view of the transfer tool of FIGS. 2A-2C in an unfolded condition showing the inner side of the transfer tool.
Figure 6:
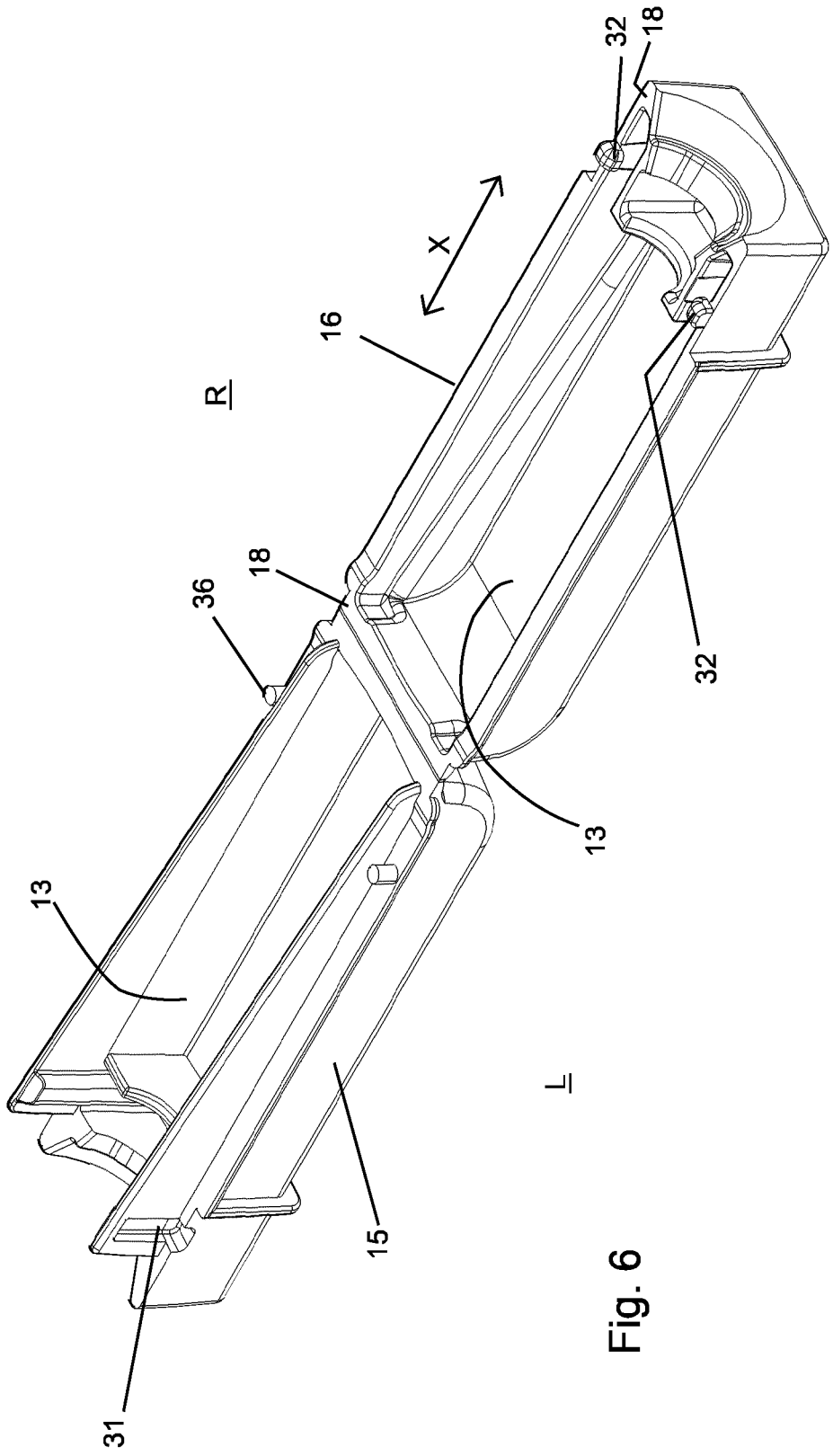
FIG. 6 shows a perspective view of the transfer tool of FIGS. 3A-3C in an unfolded condition showing the inner side of the transfer tool.
Figure 7B:
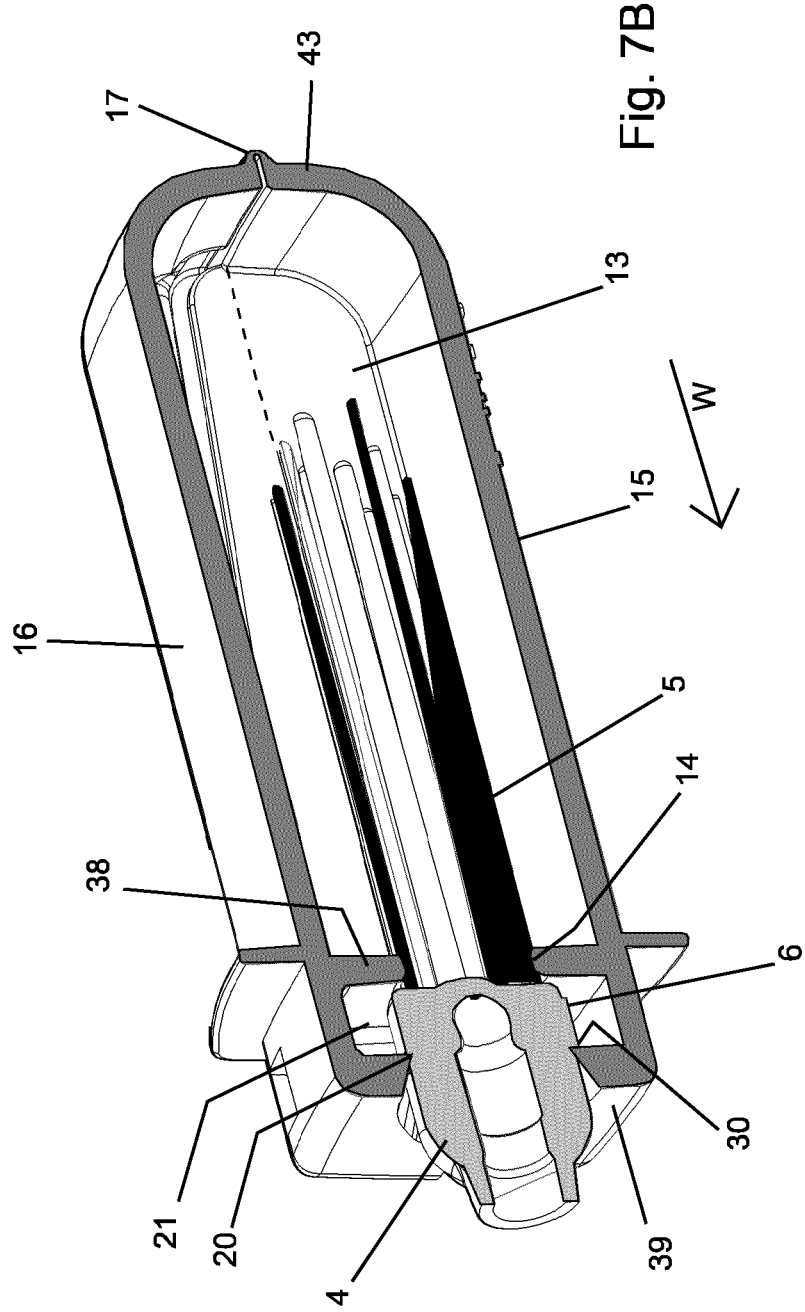

FIGS. 2 and 3 show different embodiments of a transfer tool 11 according to the invention. The difference, to be further discussed further below, is in that the transfer tool of FIG. 2 has a slit-protrusion system 31, 32 with a bumb 35 and without a tensioning element 36, whilst the transfer tool of FIG. 3 has a slit-protrusion system 31, 32 without a bumb 35 and with a tensioning element 36. For the rest, the transfer tools of the FIGS. 2-3 are in this example identical. In FIGS. 2-3 (like in the other figures as well) same reference numbers have been used for same features. FIG. 5 shows the transfer tool of FIG. 2 in a condition folded open and FIG. 6 shows the transfer tool of FIG. 3 in a condition folded open. Further FIG. 7A shows a cross-section of the transfer tool of both FIGS. 2 and 3 in 'non-holding condition' (the difference between the embodiments of these figures is not visible in this cross section) and FIG. 7B shows a cross-section of the transfer tool of both FIGS. 2 and 3 in 'holding condition' (the difference between the embodiments of these figures is not visible in this cross section). FIG. 8 shows the transfer tool of both FIGS. 2 and 3 provided with a cap 37 (the difference between the embodiments of these figures is not visible in this cross section).

Figure 2B:
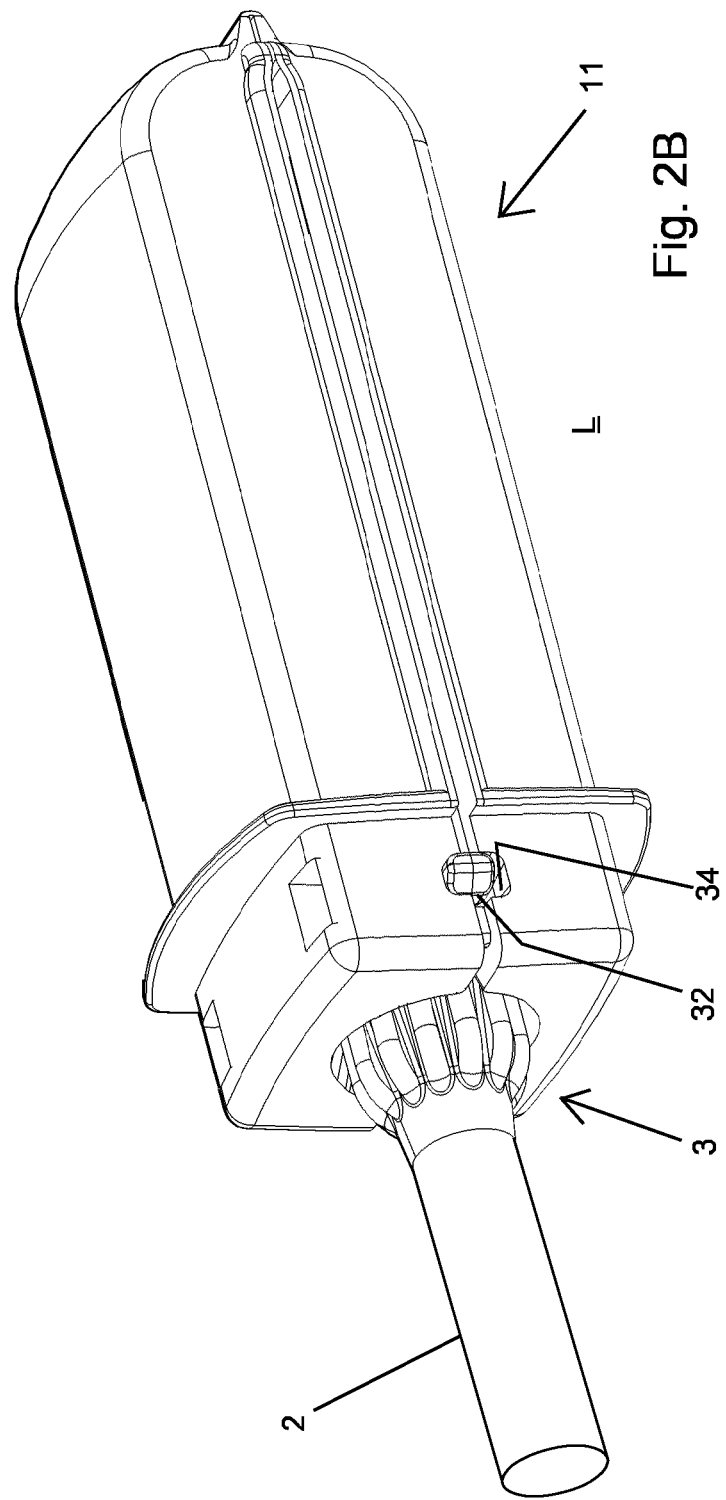
Figure 2C:
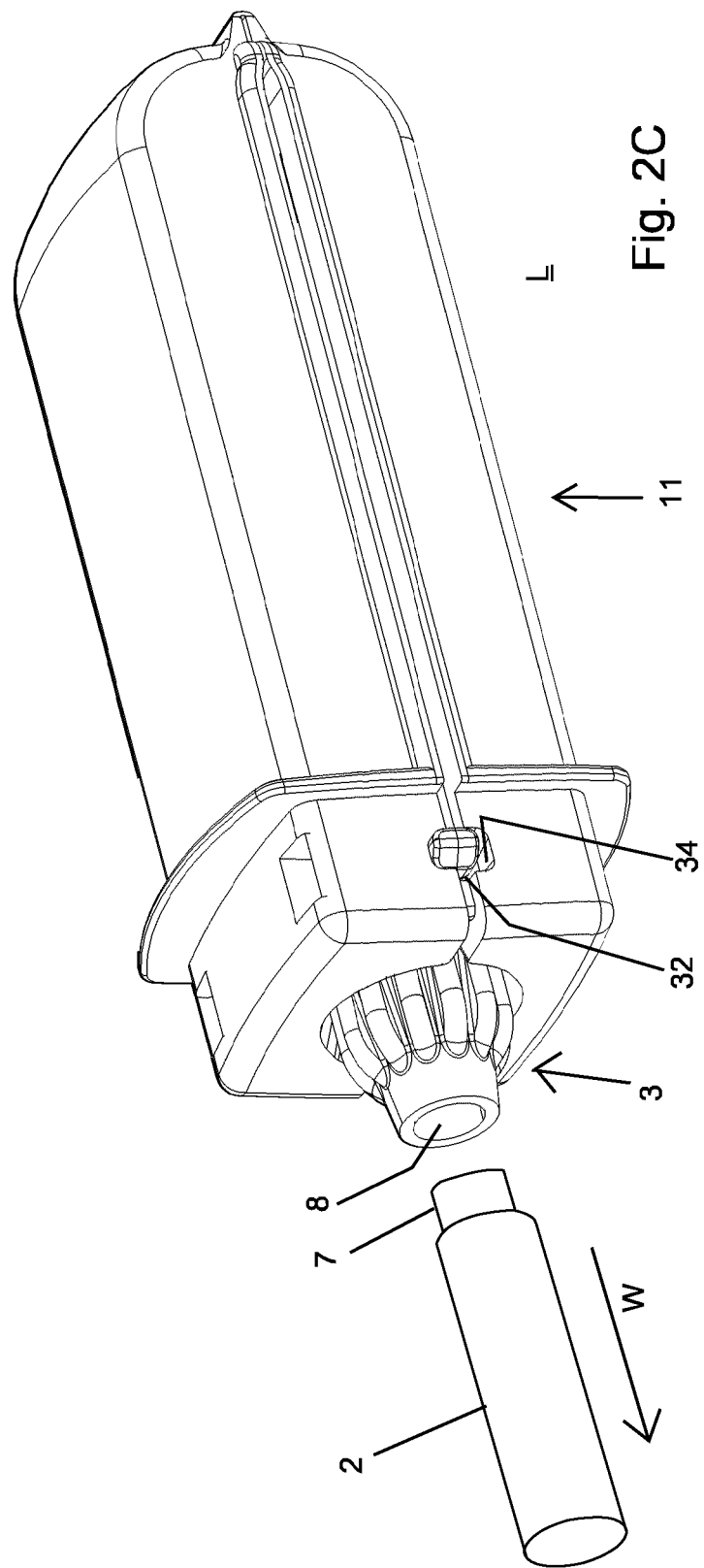
Figure 3A:
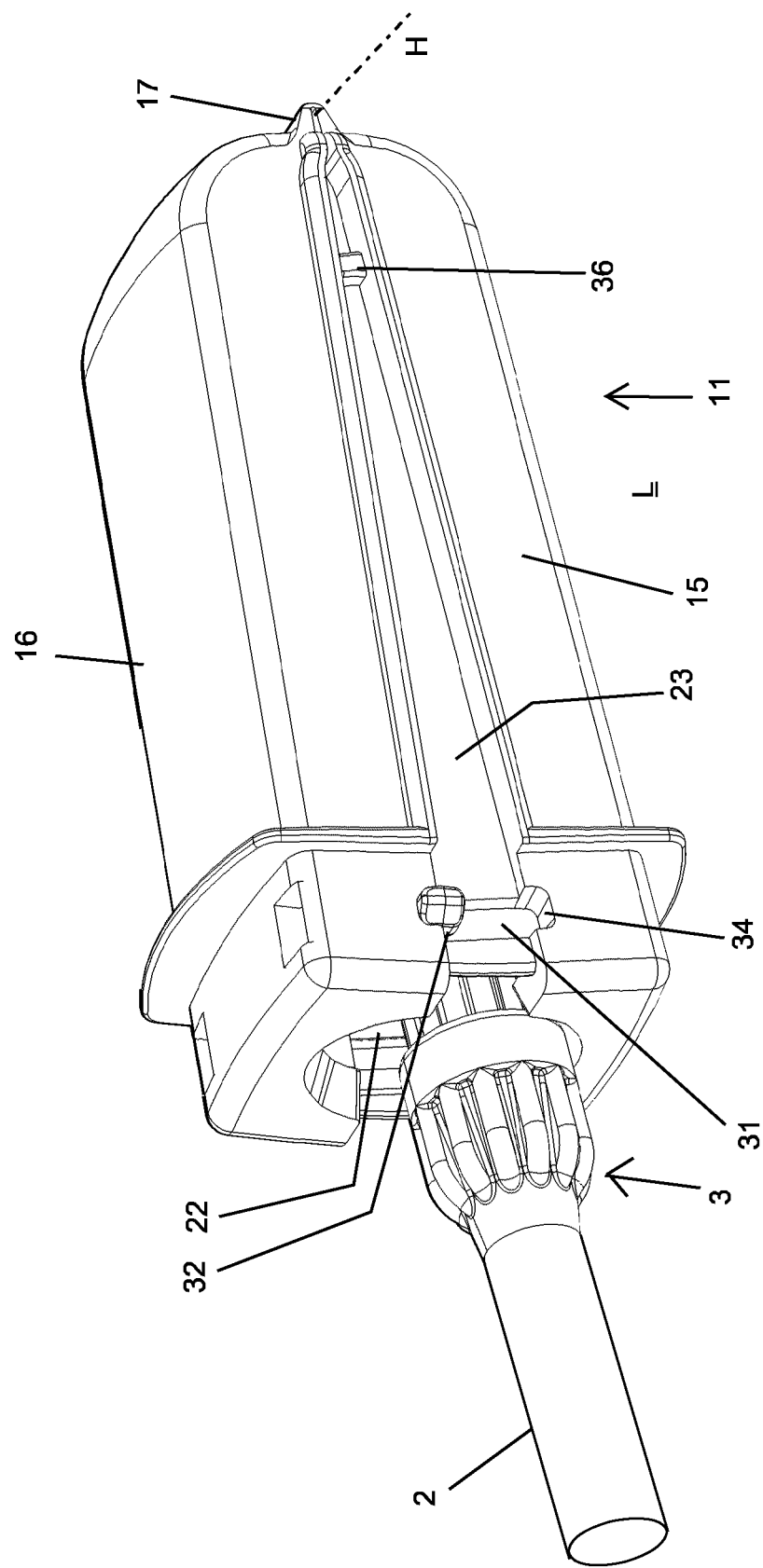
FIGS. 3A-3C show perspective views of a third embodiment of an assembly according to the invention.
Figure 3B:
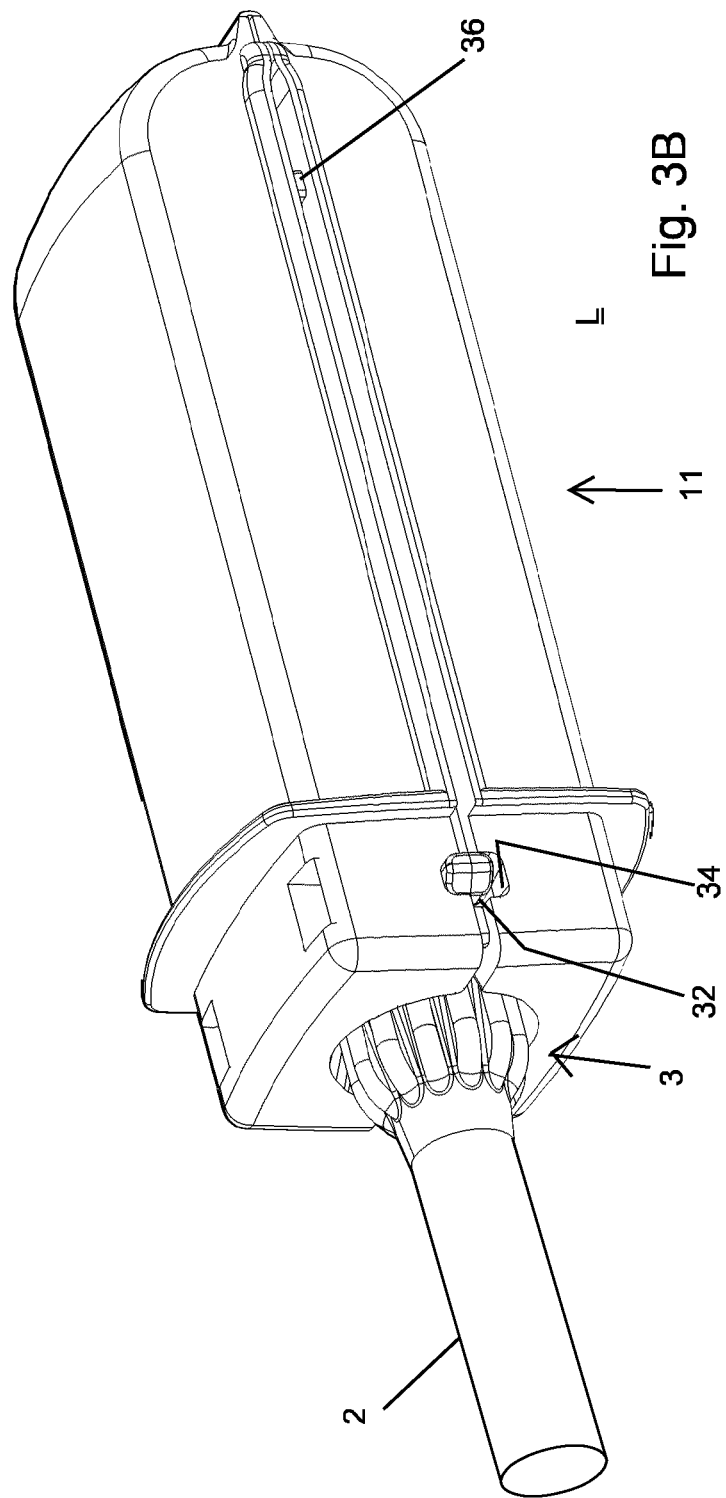
Figure 3C:
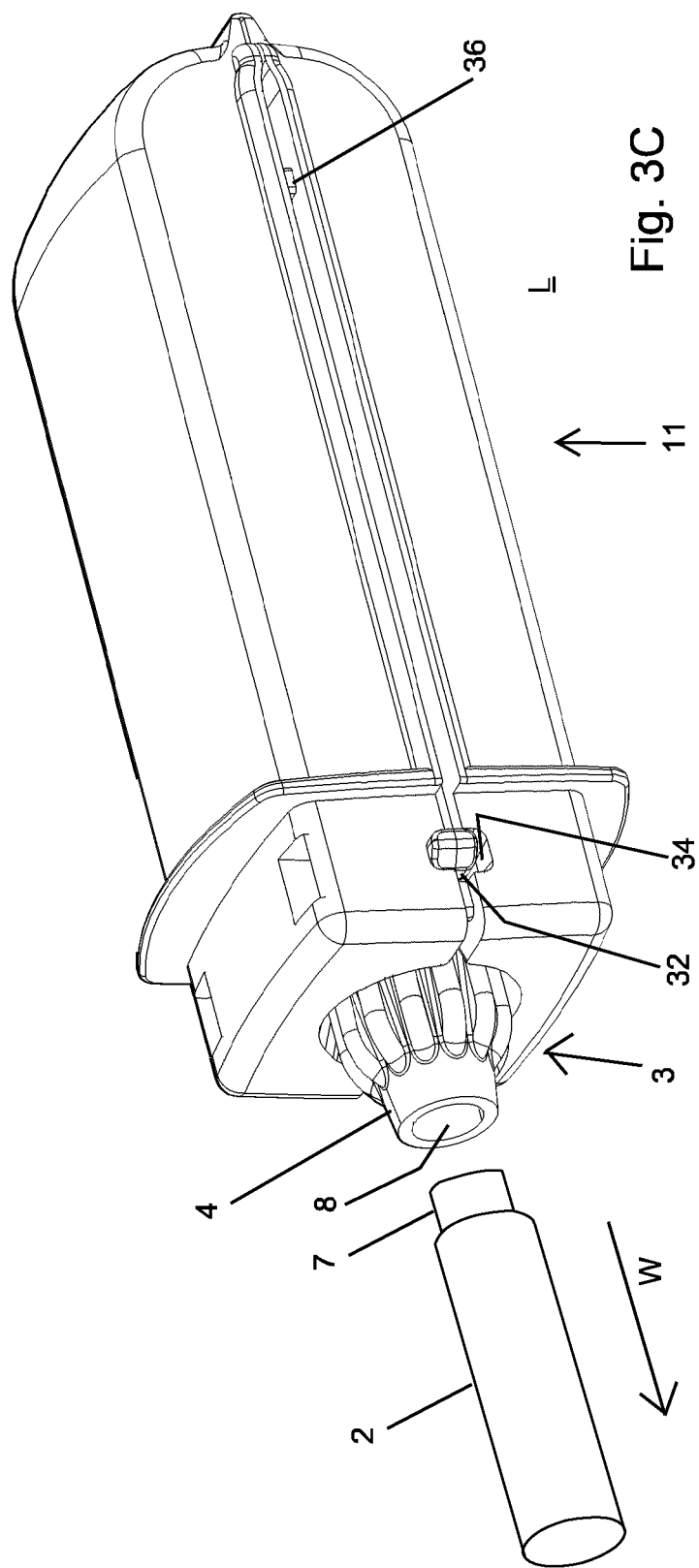

FIGS. 2 and 3, each show a transfer tool in a 'non-holding condition' (or non-holding state) whilst a swab 3 on a rod 2 is being inserted in an insertion direction I—see FIGS. 2A and 3A and 7A (without rod)—; each show a transfer tool in the 'holding condition' with a swab 3 inserted in the transfer tool 11 and the swab 3 still attached on the rod 2—see FIGS. 2B and 3B—; and each show a transfer tool in the 'holding condition' with a swab 3 inserted in the transfer tool 11 and the swab 3 detached from the rod 2—see FIGS. 2C and 3C and 7B—by withdrawing the rod 2 in the direction W from the transfer tool 11 and swab.

The transfer tool 11 according to the invention is configured to allow the first housing part 15 to rotate with respect to the second housing part 16 around a hinge axis H of a hinge 17. In case the transfer tool according to the invention has been made by injection moulding, for example as a single part, the hinge 17 may for example be a film hinge.

The rotation of the first housing part 15 with respect to the second housing part 16 is in a condition ready for use a limited one. This rotation is in a condition ready for use limited between a 'non-holding condition' as shown in FIGS. 2A, 3A and 7A and a 'holding condition' as shown in FIGS. 2B, 2C, 3B, 3C and 7B. This limited rotation may be achieved for example by means of resilient lip attached to the first housing part, the lip having a ridge which can engage into two depressions provided on the second housing part.

In the embodiment shown in FIGS. 1-8, the limited rotation of the first housing part 15 with respect to the second housing part 16 is realized by means of a movement-limiting-system, such as a slit-protrusion system. As may be seen best in FIGS. 5 and 6, the first housing part 15 is provided with a slit 31 having a first end 33 defining the 'non-holding condition' and a second end 34 defining the 'holding condition'; and the second housing part is provided with a protrusion 32 which, in a condition ready for use, projects into the slit 31. When the second housing part 16 opens with respect to the first housing part 1, further opening is blocked once the protrusion 32 reaches the first end 33 of the slit. When the second housing part 16 closes with respect to the first housing part 1, further closing is blocked once the protrusion 32 reaches the second end 34 of the slit 31. It is noted that further closing may also be achieved in different manner for example by other parts of the first 15 and second 16 housing part abutting against each other. Further, it is noted that the slit 31 and protrusion 32 may also be provided the other way around, i.e. the slit 31 being formed in the second housing part 16 and the protrusion 32 being formed on the first housing part 15. Further, it is noted that the transfer tool may be provided with one, two or more of the same or similar movement-limiting-systems. In the embodiments shown, the first 15 and second 16 housing part have a slit-protrusion system on the right side R and on the left side L.

In the embodiment of FIGS. 2 and 5, the slit is provided with a bump 35. This bump 35 is configured such that it hinders the protrusion 32 when moving back and forth through the slit, but does not prevent the protrusion 32 from passing over the bump. This may for example be realized due to flexibility of the first 15 and/or second 16 housing part, allowing the protrusion and bump 35 to move slightly with respect to each other in a direction transverse to the direction of the slit 31 and/or parallel to the hinge axis H. The bump 35 allows the transfer tool 11 to be maintained in the holding condition by preventing the protrusion 32 from movement through the slit 31. In case the transfer tool is to be move to the non-holding condition, a predetermined amount of force applied will allow the protrusion to pass over the bump 35.

In the embodiment of FIGS. 3 and 6, the slit 31 is not provided with a bump 35 but a tensioning element 36 is provided. This tensioning element 36 is configured to bias (or pretension) the first 15 and second 16 housing parts, when in the holding condition, to the non-holding condition. This bias facilitates easy bringing the transfer tool into the non-holding condition when the swab is to be released from the housing 12—as will be discussed further below in relation to figure. The tensioning element 36 to bias the first and second housing part to open when in holding condition, may according to the invention be configured in various manners. For example a spring may be arranged between the first and second housing. Another manner as shown in the FIGS. 3 and 6 is to provide an obstacle 36, like a pin, counteracting or hindering closure of the first and second housing part 15, 16. The force required to close the first and second housing part will introduce, in the first 15 and/or second 16 housing part and/or in the hinge 17, a tension resulting in a force acting in opening direction.

As can be seen in FIGS. 2C and 3C as well as FIG. 7, the connection between the rod 2 and swab 3 is, in this example, a male-female-connection. The male part 7 is provided on the end of the rod 2 and the female part 8 is provided in the base 4 of the swab. This male-female-connection may for example be by means of clamping action between the male 7 and female 8 part. The clamping action may for example be obtained by friction between the male 7 and female 8 part, or by, just another example and not shown, a rib inside the female part engaging in a corresponding recess on the male part (or the other way around a rib on the male part and a corresponding recess in the female part. In case of using a rib and corresponding recess, the connection may also be by snap action with (or without) additional clamping action. Another example to obtain the male-female-connection is using an adhesive in the male-female-connection. Still another example of a connection is a weakened, breakable transition between the rod and the swab.

Referring to FIGS. 5-7, the introduction of a swab 3 into the transfer tool 11 and the detachment of the swab 3 from the rod of a sampling device will be described more detailed.

In FIG. 7, the cutting face of the swab-member is coloured black, the cutting face of the first 15 and second 16 housing part is coloured grey, and the cutting face of the base 4 is coloured grey as well, but in a lighter shade.

As can be seen in FIGS. 7A and 7B, the housing 12 formed by the first housing part 15 and second housing part 16 has a back wall 43, a front wall 39 and an intermediate wall 38. Between the front wall 39 and intermediate wall 38 an interspace 21 is defined, which is in this application also called a channel 21. The front wall 39, intermediate wall 38 and back wall 43 are in the example shown all made of two parts, one part associated with the first housing part 15 and the other part associated with the second housing part 16. It is however also conceivable to have make one or more of these wall 38, 39, 43 from one piece. Especially, the back wall 43 may be made from one piece or the back wall 43 and intermediate wall 38 may each be made from one piece.

The intermediate wall 38 has a passage 14 allowing insertion of the swab-member 5 into and through this passage 14. The front wall 39 has an entry opening for insertion of the swab 3 into the housing 12.

The housing encloses chamber 13 delimited by the intermediate wall 38, the back wall 43 and the side walls of the first and second housing parts 15, 16 connecting the intermediate wall 38 and back wall 43. This chamber 13 is accessible through the passage 14 and further essentially closed.

As can be seen in FIG. 7A, the entry opening 20 of the channel 21—which entry opening is defined in the front wall 39—is configured to allow, in the 'non-holding condition', insertion of the swab 3, more specifically insertion of the swab-member 5 and the base 4, in an insertion direction I, from outside the housing 12 through the entry opening 20 into the channel 21; and to allow advancing the swab-member 5 and base 4 to advance further in the direction of the swab-member passage 14. This is achieved in this example by oversizing the channel 21 with respect to the cross sectional dimensions of both the swab-member 5 and the base, and by configuring the entry opening such that it is in the 'non-holding condition' oversized with respect to the cross sectional dimensions of both the swab-member 5 and the base 4. Cross sectional dimensions are in this respect defined as the dimensions transverse to the insertion direction I.

Similar the swab-member-passage 14 is configured to allow in the 'non-holding condition' insertion and passage of the swab-member 5, BUT, contrary to the configuration of the entry opening 20, the swab-member passage 14 prevents the base 4 from passing when in the 'non-holding condition'. The swab-member passage 14 blocks the base in all use conditions. This allows the swab-member to project into the chamber 13. The chamber 13 is, not only in this embodiment but in general, preferably oversized with respect to the swab-member 5 so that the swab-member is prevented from contacting the inner wall faces of the chamber 13. This facilitates preventing sample material from being dislodged from the swab member. Preventing sample material from being dislodged from the swab-member 5 is further, not only in this embodiment but in general, prevented according to a preferred embodiment by configuring the swab-member passage 14 to be, in the 'non-holding condition' oversized with respect to the cross sectional dimensions of the swab-member 5. Cross sectional dimensions are in this respect again defined as the dimensions transverse to the insertion direction I.

As can be seen in FIG. 7B, the entry opening 20 of the channel 21 is configured to prevent, in the 'holding condition'=with base at least partly inside the channel 21—the base from movement into the direction W which is opposite the insertion direction I. When the swab is inserted into the housing, the swab thus cannot be removed from the housing when the housing is in 'holding condition'. This configuration to prevent the swab from being removed from the housing when the housing is in 'holding condition', may be achieved in various manners.

Two of these manners to prevent the swab from being removed from the housing when the housing is in 'holding condition', are shown in FIG. 7A and especially FIG. 7B. For illustrative purposes, the upper side of the base 4 of the swab is configured differently than the lower side of the base of the swab. The lower side of the base 4 is provided with a wide section 6, which is somewhat wider than the part of the base on the left in the FIG. 7B. This allows a stepped transition 30 from the wide section 6 of the base to a less wide part of the base, which stepped transition 30 may catch behind the inner side of the entry opening 20 to act as a stop for the wide section 6. In the other manner, shown at the upper side of the base 4, the edge of the entry opening is, in the 'holding condition' so to say forced somewhat into the base to provide a clamping engagement, see especially FIG. 7B. These two manners may be applied separately or in combination.

In the 'holding condition' the swab-member passage may still be more or less oversized with respect to the cross sectional dimensions of the swab-member. However, not only in this embodiment but in general, the swab-member passage 14 may be configured to engage in the 'holding condition' around the swab-member to hold it into position. In addition or alternatively, not only in this embodiment but in general, the first 15 and second 16 housing part may according to the invention be configured to hold the swab in 'holding condition' of the housing motionless with respect to the housing 12. This facilitates in preventing sample material from being dislodged in the chamber from the swab-member.

FIGS. 5 and 6 further shows that the housing 12 has a length direction X extending from the first side 18 of the second housing to the second side 19 of the second housing (or vice versa). This length direction X also defines a length direction of the chamber 13 when the transfer tool is in the holding condition or in non-holding condition as is shown in FIGS. 1B, 2A, 2B, 2C, 3A, 3B, 3C, 4A, 4B, 7A, 7B and 8. As is further visible in FIGS. 5 and 6, the first housing part 15 may, according to a further embodiment of the invention, have a right side wall 22 at a right side R of the chamber 13, which right side wall extends in the length direction X perpendicular to the hinge axis H. Similarly, the first housing part has a left side wall 23 at the opposite side of the chamber 13. In this further embodiment, the second housing part 16 has a similar right side wall 24 and left side wall 25. These right side walls and second side walls are configured such that:

the right side walls 22, 24 overlap and continuously lie against each other along the full length of the chamber 13 to provide a contact seal in both the holding condition and the non-holding condition; and the left side walls 23, 25 overlap and continuously lie against each other along the full length of the chamber 13 to provide a contact seal in both the holding condition and the non-holding condition.

The contact seal along the full length of the chamber provides an effective sealing of the chamber whilst allowing movement of the first and second housing part with respect to each other. In the holding condition, this (single flat surface) sealing may be improved by providing the side walls 22, 23 or 24, 25 of either the first housing part 15 or the second housing part 16 with a right respectively left support face 26, 28 which is configured to lie, in holding condition, against a right 27 respectively left 29 length edge of either the second housing part 16 or first housing part 15. This configuration may provide an about L-shaped seal (with two mutually transverse surface sealings) in the holding condition. In addition to the second end of the slit or as an alternative for the second end of the slit, the abutting support surfaces and length edges may also define the holding condition of the transfer tool. In this embodiment with one single flat surface sealing or with two mutually transverse surface sealings, the stability of the first housing part 15 with respect to the second housing part 16 may be improved by arranging the right 22 and left 23 side wall of the first housing part 15 between the right 24 and left 25 side wall of the second housing part 16 (or the other way around by arranging the right 24 and left 25 side wall of the second housing part 16 between the right 22 and left 23 side wall of the first housing part 15).

Figure 4A:
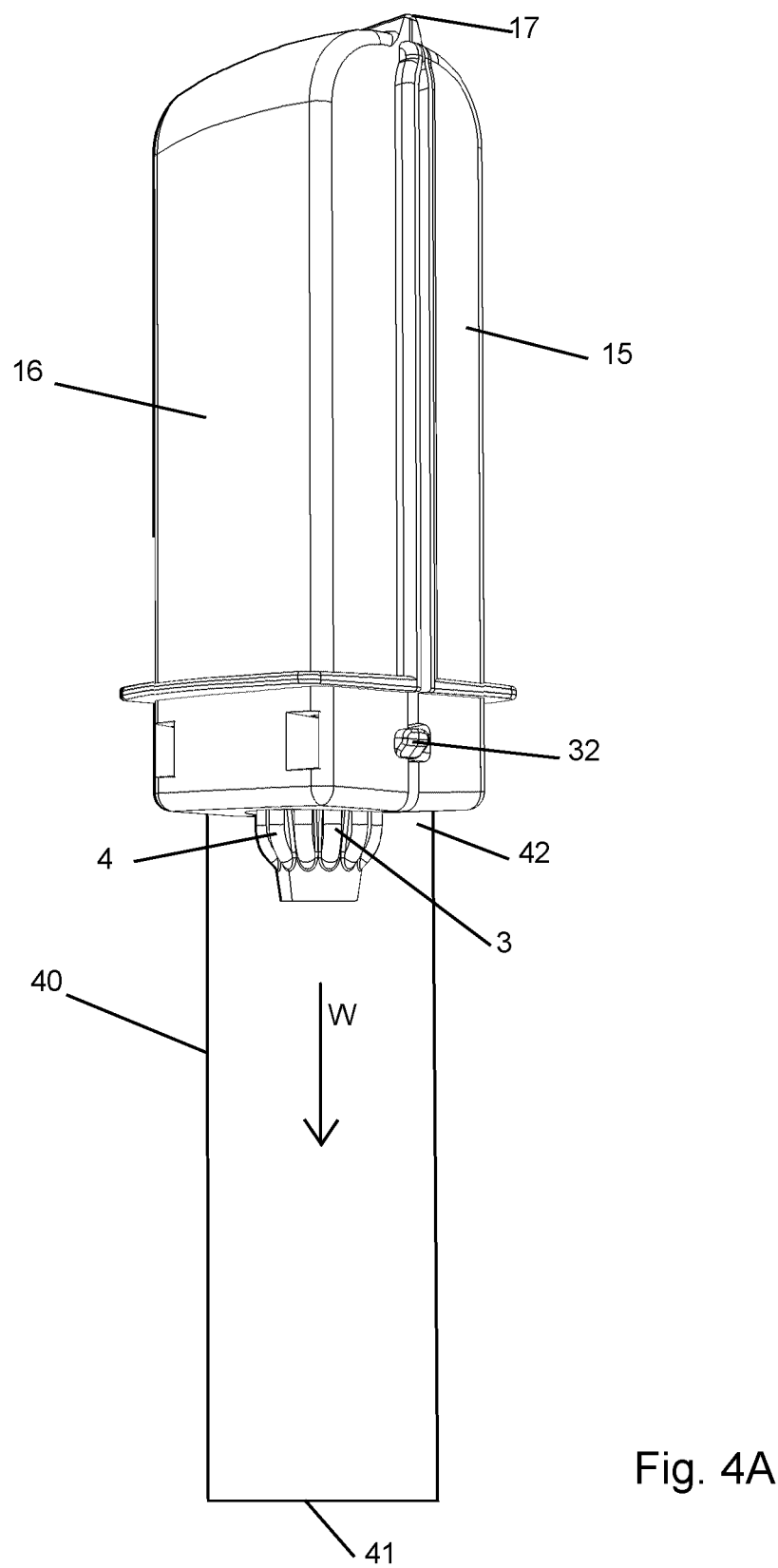
FIGS. 4A and 4B show in perspective views how with the embodiments of FIG. 1A, FIG. 1B, FIGS. 2A-2C, and FIGS. 3A-3C, the swab can be released from the transfer tool.

FIG. 4A shows a transfer tool according to invention, in holding condition and arranged above a tubular container 40 which may have a closed bottom 41 or open bottom and has an open top end 42. Can be seen a swab-member 5 is housed in the housing 12 and projects with the free end of the base 4 into the container 40.

Figure 4B:
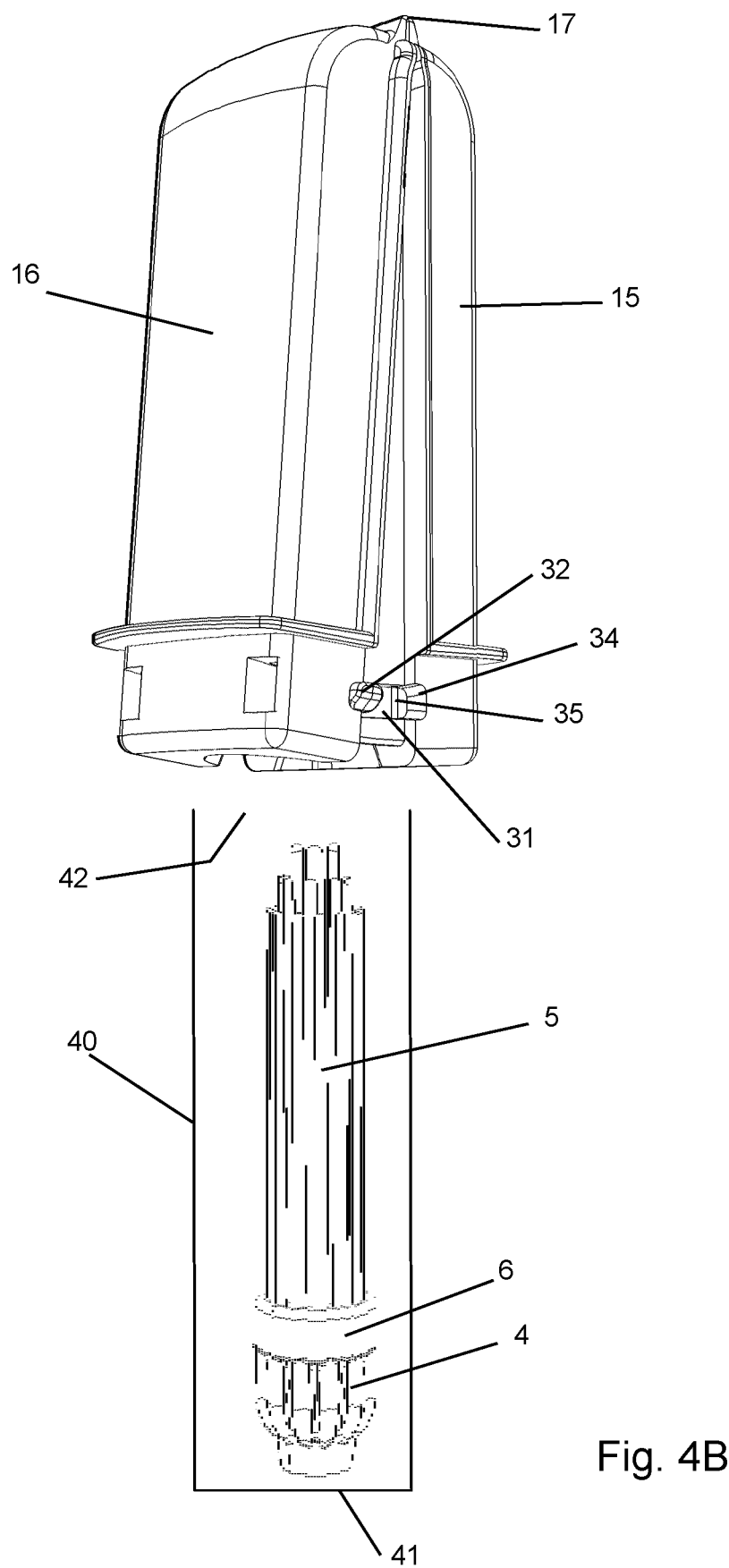

Referring to FIG. 4B, opening of the transfer tool according to the invention results in the swab-member 5 being dropped into the container 40.

Various embodiments of the invention may be represented in wording as worded in the next following clauses:

1] Assembly Comprising:

a sampling device 1 comprising a rod 2 and a swab 3, wherein the swab 3 comprises a base 4 and a swab-member 5 integral with the base 4, the base 4 being mounted on the rod 2 between the rod 2 and the swab-member 5, the sampling device 1 being configured to allow detachment of the swab 3 from the rod 2;

a transfer tool 11 for detaching the swab 3 from the rod 2 and transferring the detached swab 3 to a container 40, wherein the transfer tool 11 comprises a housing 12 enclosing a closed chamber 13, which is accessible through a swab-member passage 14 and configured for receiving the swab-member 5, the housing 12 comprising a first housing part and second housing part 16 hinged to the first housing part by a hinge 17 at a first side 18 of the second housing part 16, the first housing part and second housing part 16 defining, at a second side 19 of the second housing part 16 opposite the first side 18, an entry opening 20 to a channel 21 delimited by the first and second housing part 16, the channel 21 extending from outside the housing 12 to the swab-member passage 14;

wherein the first housing part and second housing part 16 are rotatable with respect to each other around a hinge axis H of the hinge 17 between a holding condition and a non-holding condition, wherein the swab-member passage 14 is configured to prevent, in the holding condition as well as the non-holding condition, the base 4 from entering the swab-member passage 14 whilst allowing, in the non-holding condition, the swab member to pass through the swab-member passage 14; and wherein the channel 21 and swab 3 are configured:

to allow, in the non-holding condition, inserting the swab-member 5 and the base 4, in an insertion direction I, from outside the housing 12 through the entry opening 20 into the channel 21, advancing the swab-member 5, in the insertion direction I, to and through the swab-member passage 14 into the chamber 13 until the swab-member passage 14 prevents the base 4 from entering the swab-member passage 14, and to prevent, in the holding condition whilst the swab-member passage 14 blocks the base 4 in the insertion direction I and the swab-member 5 projects through the swab-member passage 14 into the chamber 13, the base 4 from movement into a direction opposite to the insertion direction I.

2] Assembly according to clause 1, wherein the housing 12 has a length direction extending from the first side 18 to the second side 19, extending perpendicular to the hinge axis H and defining a length of the chamber 13;

wherein the first housing part 15 has, at a right side R of the chamber 13, a right side wall 22 extending in the length direction X perpendicular to the hinge axis H and, at a left side L of the chamber 13, a left side wall 23 extending in the length direction X perpendicular to the hinge axis H;

wherein the second housing part 16 has, at a right side R of the chamber 13, a right side wall 24 extending in the length direction X perpendicular to the hinge axis H and, at a left side L of the chamber 13, a left side wall 25 extending in the length direction X perpendicular to the hinge axis H;

wherein, in the holding condition as well as in the non-holding condition as well as when moving between the holding and non-holding condition and viewed transverse to the length direction X, the right side wall 22 of the first housing part 15 and the right side wall 24 of the second housing part 16 overlap and continuously lie against each other along the full length of the chamber 13 to provide a contact seal;

wherein, in the holding condition as well as in the non-holding condition as well as when moving between the holding and non-holding condition and viewed transverse to the length direction X, the left side wall 23 of the first housing part 15 and the left side wall 25 of the second housing part 16 overlap and continuously lie against each other along the full length of the chamber 13 to provide a contact seal.

3] Assembly according to clause 2, wherein, viewed transverse to the length direction X, the left and right side wall 22, 23; 24, 25 of one of the first 15 and second 16 housing part are arranged between the left and right side wall 24, 25; 22, 23 of the other of the first 15 and second 16 housing part.

4] Assembly according to one of the clauses 2-3, wherein the right side wall 22; 24 of one of the first 15 and second 16 housing part is provided with a right support face 26, which projects from that side of the respective side wall 22; 24 facing the overlapping right side wall 24; 22 of the other of the first 15 and second 16 housing part, which right support surface 26 is configured to lie:
- when in the holding condition, along the full length of the chamber 13 continuously against a right length edge 27 of the right side wall 24; 22 of the other of the first 15 and second 16 housing part, and
- when in the non-holding condition, at a distance from the right length edge, and wherein the left side wall 23; 25 of one of the first 15 and second 16 housing part is provided with a left support face 28, which projects from that side of the respective side wall 23; 25 facing the overlapping left side wall 25; 23 of the other of the first 15 and second 16 housing part, which left support surface 28 is configured to lie:
- when in the holding condition, along the full length of the chamber 13 continuously against a left length edge 29 of the left side wall 25; 23 of the other of the first 15 and second 16 housing part, and
- when in the non-holding condition, at a distance from the left length edge 29. holding the swab 3 fixed in holding condition 5] Assembly according to one of the clauses 1-4, wherein the channel 21 and base 4 are configured to prevent, when in holding condition, the base 4 from movement into the direction opposite to the insertion direction I by at least part of the base 4 being clamped inside the channel 21.

6] Assembly according to one of the clauses 1-5, wherein the base 4 has a wide section 6 which, in the direction away from the swab-member 5, reduces in wideness with a step 30, wherein the channel 21, viewed from the outside into the channel 21, widens behind the entry opening 20 to a size allowing the wide section 6 of the base 4 to be received, wherein the entry opening 20 has, in the non-holding condition, a size wider than the wide section 6 to allowing the base 4 to pass through the entry opening 20, and wherein the entry opening 20 has, in the holding condition, a size smaller than the wide section 6, preventing the wide section 6 of the base 4, when it is in the channel 21 and when the tool 11 is in the holding condition, from passing through the entry opening 20 in a direction opposite W to the insertion direction I.

7] Assembly according to one of the clauses 1-6, wherein the tool 11 comprises an slit-protrusion-system comprising a slit 31 and a protrusion 32 projecting into the slit 31, the slit 31 extending in a direction transverse to the hinge axis H and transverse to the length axis X, the protrusion 32 extending in a direction parallel to the hinge axis H, and the protrusion 32 being movable to and fro through the slit 31 between a first end 33 of the slit 31 defining to the non-holding condition and a second end 34 of the slit 31 defining the holding condition, and wherein one of the first 15 and second 16 housing part is provided with the slit 31 whilst the other of the first 15 and second 16 housing part is provided with the protrusion 32.

8] Assembly according to clause 7, wherein the tool 11 comprises two said slit-protrusion systems, one of said slit-protrusion-systems being provided on a right side R of the housing 12 and the other of said slit-protrusion-systems being provided on the left side L of the housing 12, right and left being defined with respect to a direction parallel to the hinge axis H.

9] Assembly according to one of the clauses 7-8, wherein the bottom of the slit is provided with a bump 35 configured to hinder the protrusion 32, when it is at the second end 34 of the slit 31, from movement towards the first end 33 of the slit 31 such that the protrusion 32 is prevented from leaving the second end 34 unless a predetermined force is applied to force the protrusion 32 to pass the bump 35.

10] Assembly according to one of the clauses 7-8, wherein the tool 11 comprises a tensioning element 36 configured to build up a force between the first housing part 15 and second housing part 16 when the first housing part 15 and second housing part 16 are moved from the non-holding condition to the holding condition, which force acts in a direction to return the first 15 and second 16 housing part to their non-holding condition.

11] Assembly according to one of the clauses 1-10, wherein, viewed from the outside into the channel 21, the entry opening 20 is tapered at its outside.

12] Assembly according to one of the clauses 1-11, wherein the assembly further comprises a cap 37 delimiting a cavity configured to receive the end of the housing 12 with the entry opening 20 when the housing 12 is in holding condition and to keep the housing 12 in holding condition when said end of the housing 12 has been inserted into the cavity.

13] Assembly according to clause 12, wherein the cavity has a depth and a width, and wherein the ratio of depth to width is at least 50%, such as at least 60%.

14] Assembly according to one of the clauses 12-13, wherein the cavity has a depth of at least 7 mm, such as at least about 8 or about 9 mm.

15] Assembly according to one of the clauses 1-14, wherein the container 40 is a tube with closed bottom 41 and open top end 42.

16] Assembly according to one of the clauses 1-15,
wherein the swab-member passage 14 is delimited by both a part of the first housing part 15 and a part of the second housing part 16 and configured to have in the holding condition a size smaller than in the non-holding condition such that the swab-member passage engages a part of the swab-member 5 extending within the passage 14.

17] Transfer tool 11 for detaching a swab 3 from a rod 2 and transferring the detached swab 3 to a container 40, wherein the transfer tool 11 is configured according to the transfer tool 11 of the assembly according to one of the clauses 1-16.

18] Transfer tool 11 configured for use in an assembly according to one of the clauses 1-16.

As has been described extensively, further embodiments within the scope as defined by the claims are very well conceivable.

What is claimed is:

1. An assembly comprising:
    a sampling device comprising a rod and a swab, wherein the swab comprises a base and a swab-member integral with the base, the base being mounted on the rod between the rod and the swab-member, the sampling device being configured to allow detachment of the swab from the rod;
    a transfer tool for detaching the swab from the rod and transferring the detached swab to a container,
   wherein the transfer tool comprises a housing enclosing a closed chamber, which is accessible through a swab-member passage and configured for receiving the swab-member, the housing comprising a first housing part and second housing part hinged to the first housing part by a hinge at a first side of the second housing part, the first housing part and second housing part defining, at a second side of the second housing part opposite the first side, an entry opening to a channel delimited by the first and second housing parts, the channel extending from outside the housing to the swab-member passage;
   wherein the first housing part and second housing part are rotatable with respect to each other around a hinge axis of the hinge between a holding condition and a non-holding condition,
   wherein the swab-member passage is configured to prevent, in the holding condition as well as the non-holding condition, the base from entering the swab-member passage whilst allowing, in the non-holding condition, the swab-member to pass through the swab-member passage; and
   wherein the channel and swab are configured:
      to allow, in the non-holding condition, inserting the swab-member and the base, in an insertion direction, from outside the housing through the entry opening into the channel, advancing the swab-member, in the insertion direction, to and through the swab-member passage into the chamber until the swab-member passage prevents the base from entering the swab-member passage, and
      to prevent, in the holding condition whilst the swab-member passage blocks the base in the insertion direction and the swab-member projects through the swab-member passage into the chamber, the base from movement into a direction opposite to the insertion direction.

2. The assembly according to claim 1,
   wherein the housing has a length direction extending from the first side to the second side, and defining a length of the chamber;
   wherein the first housing part has, at a right side of the chamber, a right side wall extending in the length direction perpendicular to the hinge axis and, at a left side of the chamber, a left side wall extending in the length direction perpendicular to the hinge axis;
   wherein the second housing part has, at a right side of the chamber, a right side wall extending in the length direction perpendicular to the hinge axis and, at a left side of the chamber, a left side wall extending in the length direction perpendicular to the hinge axis;
   wherein, in the holding condition as well as in the non-holding condition as well as when moving between the holding and non-holding conditions and viewed transverse to the length direction, the right side wall of the first housing part and the right side wall of the second housing part overlap and continuously lie against each other along the full length of the chamber to provide a contact seal;
   wherein, in the holding condition as well as in the non-holding condition as well as when moving between the holding and non-holding conditions and viewed transverse to the length direction, the left side wall of the first housing part and the left side wall of the second housing part overlap and continuously lie against each other along the full length of the chamber to provide a contact seal.

3. The assembly according to claim 2,
   wherein, viewed transverse to the length direction, the left and right side walls of one of the first and second housing parts are arranged between the left and right side walls of the other of the first and second housing parts.

4. The assembly according to claim 2,
   wherein the right side wall of one of the first and second housing parts is provided with a right support face, which projects from that side of the respective side wall facing the overlapping right side wall of the other of the first and second housing parts, which right support surface is configured to lie:
      when in the holding condition, along the full length of the chamber continuously against a right length edge of the right side wall of the other of the first and second housing parts, and
      when in the non-holding condition, at a distance from the right length edge, and
   wherein the left side wall of one of the first and second housing parts is provided with a left support face, which projects from that side of the respective side wall facing the overlapping left side wall of the other of the first and second housing parts, which left support surface is configured to lie:
      when in the holding condition, along the full length of the chamber continuously against a left length edge of the left side wall of the other of the first and second housing parts, and
      when in the non-holding condition, at a distance from the left length edge.

5. The assembly according to claim 1,
   wherein the channel and base are configured to prevent, when in holding condition, the base from movement into the direction opposite to the insertion direction by at least part of the base being clamped inside the channel.

6. The assembly according to claim 1,
   wherein the base has a wide section which, in the direction away from the swab-member, reduces in wideness with a step, wherein the channel, viewed from the outside into the channel, widens behind the entry opening to a size allowing the wide section of the base to be received, wherein the entry opening has, in the non-holding condition, a size wider than the wide section to allowing the base to pass through the entry opening, and wherein the entry opening has, in the holding condition, a size smaller than the wide section, preventing the wide section of the base, when it is in the channel and when the transfer tool is in the holding condition, from passing through the entry opening in a direction opposite to the insertion direction.

7. The assembly according to claim 1,
wherein the housing has a length direction,
wherein the transfer tool comprises a slit-protrusion-system comprising a slit and a protrusion projecting into the slit, the slit extending in a direction transverse to the hinge axis and transverse to the length direction, the protrusion extending in a direction parallel to the hinge axis, and the protrusion being movable to and fro through the slit between a first end of the slit defining to the non-holding condition and a second end of the slit defining the holding condition, and
wherein one of the first and second housing parts is provided with the slit whilst the other of the first and second housing parts is provided with the protrusion.

8. The assembly according to claim 7,
wherein the transfer tool comprises two said slit-protrusion systems, one of said slit-protrusion-systems being provided on a right side of the housing and the other of said slit-protrusion-systems being provided on a left side of the housing, right and left being defined with respect to a direction transverse to the hinge axis.

9. The assembly according to claim 7,
wherein a bottom of the slit is provided with a bump configured to hinder the protrusion, when it is at the second end of the slit, from movement towards the first end of the slit such that the protrusion is prevented from leaving the second end unless a predetermined force is applied to force the protrusion to pass the bump.

10. The assembly according to claim 7,
wherein the transfer tool comprises a tensioning element configured to build up a force between the first housing part and second housing part when the first housing part and second housing part are moved from the non-holding condition to the holding condition, which force acts in a direction to return the first and second housing parts to their non-holding condition.

11. The assembly according to claim 1,
wherein, viewed from the outside into the channel, the entry opening is tapered at its outside.

12. The assembly according to claim 1,
wherein the assembly further comprises a cap delimiting a cavity configured to receive an end of the housing with the entry opening when the housing is in holding condition and to keep the housing in holding condition when said end of the housing has been inserted into the cavity.

13. The assembly according to claim 12, wherein the cavity has a depth and a width, and wherein a ratio of the depth to the width is at least 50%.

14. The assembly according to claim 12, wherein the cavity has a depth of at least 7 mm.

15. The assembly according to claim 1, wherein the container is a tube with a closed bottom end and an open top end.

16. The assembly according to claim 1, wherein the swab-member passage is delimited by both a part of the first housing part and a part of the second housing part and configured to have in the holding condition a size smaller than in the non-holding condition such that the swab-member passage engages a part of the swab-member extending within the swab-member passage.

17. The assembly according to claim 12, wherein the cavity has a depth and a width, and wherein a ratio of the depth to the width is at least 60%.

18. The assembly according to claim 12, wherein the cavity has a depth of at least 8 mm.

19. The assembly according to claim 12, wherein the cavity has a depth of at least 9 mm.

* * * * *